(12) United States Patent
Kim et al.

(10) Patent No.: US 7,939,230 B2
(45) Date of Patent: May 10, 2011

(54) OVERCOAT LAYER COMPRISING CORE-SHELL FLUORINATED PARTICLES

(75) Inventors: Woo Soo Kim, Oakville (CA); Nan-Xing Hu, Oakville (CA); Jennifer A. Coggan, Kitchener (CA); Yvan Gagnon, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/553,887

(22) Filed: Sep. 3, 2009

(65) Prior Publication Data

US 2011/0053064 A1  Mar. 3, 2011

(51) Int. Cl.
*G03G 5/047* (2006.01)
*G03G 5/147* (2006.01)

(52) U.S. Cl. ............ 430/58.8; 430/59.4; 430/59.1; 430/66; 430/58.05; 399/159

(58) Field of Classification Search .......... 430/58.8, 430/59.4, 66, 58.05, 59.1; 399/159
See application file for complete search history.

(56) References Cited

U.S. PATENT DOCUMENTS

| | | |
|---|---|---|
| 3,121,006 A | 2/1964 | Middleton et al. |
| 4,286,033 A | 8/1981 | Neyhart et al. |
| 4,291,110 A | 9/1981 | Lee |
| 4,338,387 A | 7/1982 | Hewitt |
| 4,387,980 A | 6/1983 | Ueno et al. |
| 4,464,450 A | 8/1984 | Teuscher |
| 4,587,189 A | 5/1986 | Hor et al. |
| 4,664,995 A | 5/1987 | Horgan et al. |
| 4,921,773 A | 5/1990 | Melnyk et al. |
| 5,153,094 A | 10/1992 | Kazmaier et al. |
| 5,166,339 A | 11/1992 | Duff et al. |
| 5,189,155 A | 2/1993 | Mayo et al. |
| 5,189,156 A | 2/1993 | Mayo et al. |
| 5,215,839 A | 6/1993 | Yu |
| 5,436,701 A * | 7/1995 | Shimojo et al. ........ 430/66 |
| 5,582,943 A * | 12/1996 | Kato et al. ............ 430/66 |
| 5,660,961 A | 8/1997 | Yu |
| 5,756,245 A | 5/1998 | Esteghamatian et al. |
| 5,958,638 A | 9/1999 | Katayama et al. |
| 6,365,309 B1 * | 4/2002 | Tokutake et al. ......... 430/67 |
| 6,964,834 B2 * | 11/2005 | Ueda et al. ............ 430/59.6 |
| 2001/0012594 A1* | 8/2001 | Ri et al. ............... 430/58.7 |
| 2008/0160438 A1 | 7/2008 | Nishina et al. |
| 2008/0166643 A1 | 7/2008 | Bender et al. |
| 2009/0081569 A1* | 3/2009 | Miyamoto et al. ......... 430/66 |

FOREIGN PATENT DOCUMENTS

| | | | |
|---|---|---|---|
| EP | 2098913 A1 | | 9/2009 |
| JP | 2003149848 A | * | 5/2003 |
| JP | 2003228188 A | * | 8/2003 |
| WO | WO 2006/098351 A1 | * | 9/2006 |

OTHER PUBLICATIONS

EP Search Report dated Dec. 10, 2010, EP Application No, 10174150.2, 7 pages.

* cited by examiner

*Primary Examiner* — Christopher RoDee
(74) *Attorney, Agent, or Firm* — Pillsbury Winthrop Shaw Pittman LLP (57) ABSTRACT

The presently disclosed embodiments are directed generally to an improved electrophotographic imaging member in which the overcoat layer incorporates core-shell fluorinated nano- or micro-particles encapsulated in a melamine shell to reduce torque and cleaning failures during the photoreceptor cleaning process.

18 Claims, 4 Drawing Sheets

OVERCOAT LAYER COMPRISING CORE-SHELL FLUORINATED PARTICLES

CROSS REFERENCE TO RELATED APPLICATIONS

Reference is made to commonly owned and co-pending, U.S. patent application Ser. No. 12/553,924 to Kim et al., the entire disclosure of which are incorporated herein by reference in its entirety.

BACKGROUND

The presently disclosed embodiments relate generally to layers that are useful in imaging apparatus members and components, for use in electrophotographic, including digital, apparatuses. More particularly, the embodiments pertain to an improved electrophotographic imaging member incorporating core-shell fluorinated particles into the overcoat layer to reduce torque and cleaning failures during the photoreceptor cleaning process. In specific embodiments, the core-shell fluorinated particles are of nano- or micro-size. The present embodiments also pertain to methods for making the core-shell fluorinated particles. In particular embodiments where the outer layer is the charge transport layer, the core-shell fluorinated particles can be incorporated into the charge transport layer instead.

In electrophotographic or electrophotographic printing, the charge retentive surface, typically known as a photoreceptor, is electrostatically charged, and then exposed to a light pattern of an original image to selectively discharge the surface in accordance therewith. The resulting pattern of charged and discharged areas on the photoreceptor form an electrostatic charge pattern, known as a latent image, conforming to the original image. The latent image is developed by contacting it with a finely divided electrostatically attractable powder known as toner. Toner is held on the image areas by the electrostatic charge on the photoreceptor surface. Thus, a toner image is produced in conformity with a light image of the original being reproduced or printed. The toner image may then be transferred to a substrate or support member (e.g., paper) directly or through the use of an intermediate transfer member, and the image affixed thereto to form a permanent record of the image to be reproduced or printed. Subsequent to development, excess toner left on the charge retentive surface is cleaned from the surface. The process is useful for light lens copying from an original or printing electronically generated or stored originals such as with a raster output scanner (ROS), where a charged surface may be imagewise discharged in a variety of ways.

The described electrophotographic copying process is well known and is commonly used for light lens copying of an original document. Analogous processes also exist in other electrophotographic printing applications such as, for example, digital laser printing or ionographic printing and reproduction where charge is deposited on a charge retentive surface in response to electronically generated or stored images.

To charge the surface of a photoreceptor, a non-contact charging device with a scorotron has been widely employed in the prior art. For office environment, a contact type charging device has also been used to charge the surface of a photoreceptor. The contact type charging device includes a conductive member which is supplied a voltage from a power source with a D.C. voltage superimposed with a A.C. voltage of no less than twice the level of the D.C. voltage. The charging device contacts the image bearing member (photoreceptor) surface, which is a member to be charged. The outer surface of the image bearing member is charged with the rubbing friction at the contact area. The contact type charging device charges the image bearing member to a predetermined potential. Typically the contact type charger is in the form of a roll charger such as that disclosed in U.S. Pat. No. 4,387,980, the relative portions thereof incorporated herein by reference.

Multilayered photoreceptors or imaging members have at least two layers, and may include a substrate, a conductive layer, an optional undercoat layer (sometimes referred to as a "charge blocking layer" or "hole blocking layer"), an optional adhesive layer, a photogenerating layer (sometimes referred to as a "charge generation layer," "charge generating layer," or "charge generator layer"), a charge transport layer, and an optional overcoating layer in either a flexible belt form or a rigid drum configuration. In the multilayer configuration, the active layers of the photoreceptor are the charge generation layer (CGL) and the charge transport layer (CTL). Enhancement of charge transport across these layers provides better photoreceptor performance. Multilayered flexible photoreceptor members may include an anti-curl layer on the backside of the substrate, opposite to the side of the electrically active layers, to render the desired photoreceptor flatness.

Print defects due to cleaning failure are one of the main issues in xerographic sub-systems. Such defects are typically observed when a low wear overcoated photoreceptor is used. For example, the defects often occur at a very early stage and is caused by blade damage and non-uniform wear of photoreceptor due to high friction and poor interactions between the cleaning blade and the photoreceptor. Further, high torque remains another issue associated with overcoat photoreceptors. Thus, there is a need for an improved imaging layer that achieves extended service lifetime and does not suffer from the above-described problems.

Conventional photoreceptors are disclosed in the following patents, a number of which describe the presence of light scattering particles in the undercoat layers: Yu, U.S. Pat. No. 5,660,961; Yu, U.S. Pat. No. 5,215,839; and Katayama et al., U.S. Pat. No. 5,958,638. The term "photoreceptor" or "photoconductor" is generally used interchangeably with the terms "imaging member." The term "electrophotographic" includes "electrophotographic" and "xerographic." The terms "charge transport molecule" are generally used interchangeably with the terms "hole transport molecule."

SUMMARY

According to aspects illustrated herein, there is a provided an imaging member comprising a substrate, an imaging layer disposed on the substrate, and an outer layer disposed on the imaging layer, wherein the outer layer further comprises a plurality of core-shell fluorinated particles comprising a fluoro-polymer core having a polymeric shell disposed on the fluoro-polymer core.

Another embodiment provides an imaging forming apparatus comprising an imaging member further comprising a substrate, an imaging layer disposed on the substrate, and an outer layer disposed on the imaging layer, a charging unit that applies electrostatic charge on the imaging member, a developing unit that develops toner image onto the imaging member; a transfer unit that transfers the toner image from the imaging member to a media; and a cleaning unit that cleans the imaging member, wherein the outer layer of the imaging member further comprises a plurality of core-shell fluorinated particles comprising a fluoro-polymer core having a polymeric shell disposed on the fluoro-polymer core.

Yet another embodiment provides an image forming apparatus wherein the overcoat layer was formed from an overcoat solution comprising core-shell fluorinated particles suspended in hydroxyl-containing fluorinated dispersants and further wherein the overcoat layer exhibits substantially less torque than an overcoat layer without the core-shell fluorinated particles.

BRIEF DESCRIPTION OF THE DRAWINGS

For a better understanding, reference may be made to the accompanying figures.

DETAILED DESCRIPTION

In the following description, reference is made to the accompanying drawings, which form a part hereof and which illustrate several embodiments. It is understood that other embodiments may be used and structural and operational changes may be made without departure from the scope of the present disclosure.

The presently disclosed embodiments are directed generally to an improved electrophotographic imaging member in which the overcoat layer incorporates core-shell fluorinated particles, and methods for making the same. These imaging members exhibit substantially reduced torque and print defects due to cleaning failures.

In electrophotographic reproducing or digital printing apparatuses using a photoreceptor, a light image is recorded in the foi in of an electrostatic latent image upon a photosensitive member and the latent image is subsequently rendered visible by the application of a developer mixture. The developer, having toner particles contained therein, is brought into contact with the electrostatic latent image to develop the image on an electrophotographic imaging member which has a charge-retentive surface. The developed toner image can then be transferred to a copy substrate, such as paper, that receives the image via a transfer member.

The exemplary embodiments of this disclosure are described below with reference to the drawings. The specific terms are used in the following description for clarity, selected for illustration in the drawings and not to define or limit the scope of the disclosure. The same reference numerals are used to identify the same structure in different figures unless specified otherwise. The structures in the figures are not drawn according to their relative proportions and the drawings should not be interpreted as limiting the disclosure in size, relative size, or location. In addition, though the discussion will address negatively charged systems, the imaging members of the present disclosure may also be used in positively charged systems.

Figure 1:
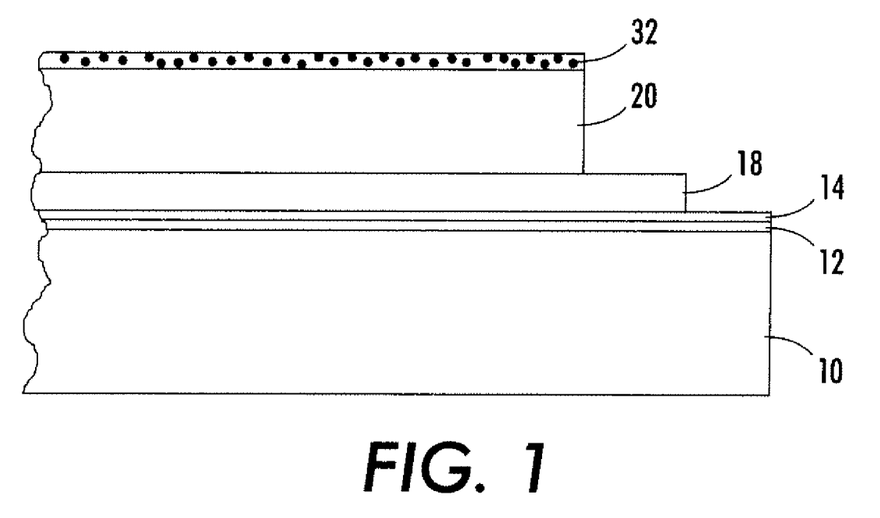
FIG. 1 is a cross-sectional view of an imaging member in a drum configuration according to the present embodiments.

FIG. 1 is an exemplary embodiment of a multilayered electrophotographic imaging member having a drum configuration. As can be seen, the exemplary imaging member includes a rigid support substrate 10, an electrically conductive ground plane 12, an undercoat layer 14, a charge generation layer 18 and a charge transport layer 20. The rigid substrate may be comprised of a material selected from the group consisting of a metal, metal alloy, aluminum, zirconium, niobium, tantalum, vanadium, hafnium, titanium, nickel, stainless steel, chromium, tungsten, molybdenum, and mixtures thereof. The charge generation layer 18 and the charge transport layer 20 forms an imaging layer described here as two separate layers. In an alternative to what is shown in the figure, the charge generation layer may also be disposed on top of the charge transport layer. It will be appreciated that the functional components of these layers may alternatively be combined into a single layer.

The Overcoat Layer

Other layers of the imaging member may include, for example, an optional over coat layer 32. An optional overcoat layer 32, if desired, may be disposed over the charge transport layer 20 to provide imaging member surface protection as well as improve resistance to abrasion. In embodiments, the overcoat layer 32 may have a thickness ranging from about 0.1 micron to about 10 microns or from about 1 micron to about 10 microns, or in a specific embodiment, about 3 microns. These overcoating layers may include thermoplastic organic polymers or inorganic polymers that are electrically insulating or slightly semi-conductive. For example, overcoat layers may be fabricated from a dispersion including a particulate additive in a resin. Suitable particulate additives for overcoat layers include metal oxides including aluminum oxide, or non-metal oxides including silica. Suitable resins include those described above as suitable for photogenerating layers and/or charge transport layers, for example, polyvinyl acetates, polyvinylbutyrals, polyvinylchlorides, vinylchloride and vinyl acetate copolymers, carboxyl-modified vinyl chloride/vinyl acetate copolymers, hydroxyl-modified vinyl chloride/vinyl acetate copolymers, carboxyl- and hydroxyl-modified vinyl chloride/vinyl acetate copolymers, polyvinyl alcohols, polycarbonates, polyesters, polyurethanes, polystyrenes, polybutadienes, polysulfones, polyarylethers, polyarylsulfones, polyethersulfones, polyethylenes, polypropylenes, polymethylpentenes, polyphenylene sulfides, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, poly-N-vinylpyrrolidinones, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazoles, and combinations thereof. Overcoating layers may be continuous and have a thickness of at least about 0.5 micron, or no more than 10 microns, and in further embodiments have a thickness of at least about 2 microns, or no more than 6 microns.

Incorporating micron-sized PTFE, particles into known overcoat formulations offers an efficient manner to reduce friction between photoreceptor and cleaning blade. However, to prepare stable coating solution comprising fluorinated particles has been a challenge as the particles tends to aggregate to form larger agglomerates which may impact the coating quality. Stable coating dispersions are thus facilitated by incorporating core-shell fluorinated particles 36, such as for example, core-shell TEFLON or PTFE nano- or micro-particles, into the overcoat layer 32. The core-shell particles 36 have a polymeric shell made of melamine resin surrounding the fluoro-polymer core. Overcoat layers having such com- positions have shown to provide longer service life as well as avoid print defects due to cleaning failures.

The core-shell fluorinated particles shows well-dispersed behavior in the overcoat formulation, good coating quality, and no negative electrical effect. Such overcoat layers filled with the core-shell fluorinated particles offer lower friction with cleaning blade, improved print quality, and smoother interaction to minimize blade damage. In embodiments, the core-shell fluorinated particles are present in an amount of from about 0.5% to about 10% by weight of the total weight of the overcoat layer, or from about 1% to about 10% by weight of the total weight of the overcoat layer.

The core-shell fluorinated particles are prepared by forming a polymeric shell around a fluoro-polymer core having a polymeric shell. The preparation involves mixing fluoro-polymer core particles in a solvent containing a hydroxyl-containing fluorinated dispersant and a curing agent to form a suspension, and polymerizing the curing agent on the surface of the core particles in the presence of an optional catalyst to form a polymeric shell around the fluoro-polymer core particles. The polymerization of the curing resin may be, in embodiments, induced at a temperature range of from about 20 degree Celsius to about 80 degree Celsius.

In embodiments, the fluoro-polymer comprises a polymer having at least a monomer repeat unit selected from the group consisting of tetrafluoroethylene, vinylidene fluoride, hexafluoropropylene, perfluoro(methyl vinyl ether), perfluoro(ethyl vinyl ether), perfluoro(propyl vinyl ether), and the like, and mixtures thereof. The fluoro-polymer may be selected from a group consisting of polytetrafluoroethylene (PTFE), perfluoroalkoxy polymer resin (PFA), a copolymer of tetrafluoroethylene (TFE) and hexafluoropropylene (HFP), a copolymer of hexafluoropropylene (HFP) and vinylidene fluoride (VDF), a copolymer of hexafluoropropylene (HFP) and vinylidene fluoride (VF2), a terpolymer of tetrafluoroethylene (TFE), vinylidene fluoride (VDF), and hexafluoropropylene (HFP), and a tetrapolymer of tetrafluoroethylene (TFE), vinylidene fluoride (VF2), hexafluoropropylene (HEP), and the like.

In embodiments, the hydroxyl-containing fluorinated dispersant comprises a polyacrylate polymer containing a hydroxyl and a fluoroalkyl group having from about 6 to about 20 carbons. In a particular embodiment, the hydroxyl-containing fluorinated dispersant has the following structure:

wherein R represents an alkyl fluorocarbon group having from about 6 to about 30 carbon atoms.

In embodiments, the curing resin is selected from a group consisting of melamine-formaldehyde resin, phenol-formaldehyde resin, melamine-phenol-formaldehyde resin, guanamine-formaldehyde resin, an isocyanate compound or a masking isocyanate compound, a polyol resin, and the like, and mixtures thereof. In the case that a catalyst is used, the catalyst may comprise an acid catalyst comprising an organosulfonic acid or its organoamine salt. In embodiments, the solvent is selected from the group consisting of an alcohol, a ketone, ether, acetate, a hydrocarbon, and the like, and mixtures thereof.

In specific embodiments, the resulting core-shell fluorinated particles have a diameter size of from about 10 nanometers to about 100 microns. In further embodiments, the core-shell fluorinated particles comprise a fluoro-polymer core with a diameter size ranging from about 20 nanometers to about 8 microns and a polymeric shell with a thickness of from about 10 nanometers to about 2 microns, or from about 10 nanometers to about 1 microns. The resulting core-shell particles are used to form an outer layer of an imaging member.

In embodiments, there is provided a process for preparing an outer layer of an imaging member, the imaging member comprising a substrate, an imaging layer disposed on the substrate, and an outer layer disposed on the imaging layer, wherein the process comprises providing an imaging member comprising a substrate and an imaging layer disposed on the substrate, providing a outer layer solution comprising a charge transport compound, a polymer resin, a solvent, and a plurality of core-shell fluorinated particles further comprising a fluoro-polymer core having a polymeric shell disposed on the fluoro-polymer core, and applying the outer layer solution onto the imaging layer to form an outer layer comprising core-shell fluorinated particles dispersed therein. In some embodiments, the process may further comprise thermal curing of the coated out layer coating.

In the above embodiment, the charge transport compound may further comprise a curable functional group selected from the group consisting of a hydroxyl, a hydroxymethyl, an alkoxymethyl, a hydroxyalkyl having from about 1 to about 15 carbons, an acrylate, and the like, and mixtures thereof. The core-shell polytetrafluoroethylene particles may be present in an amount of from about 1% to about 10% by weight of total weight of the outer layer.

Figure 2A:
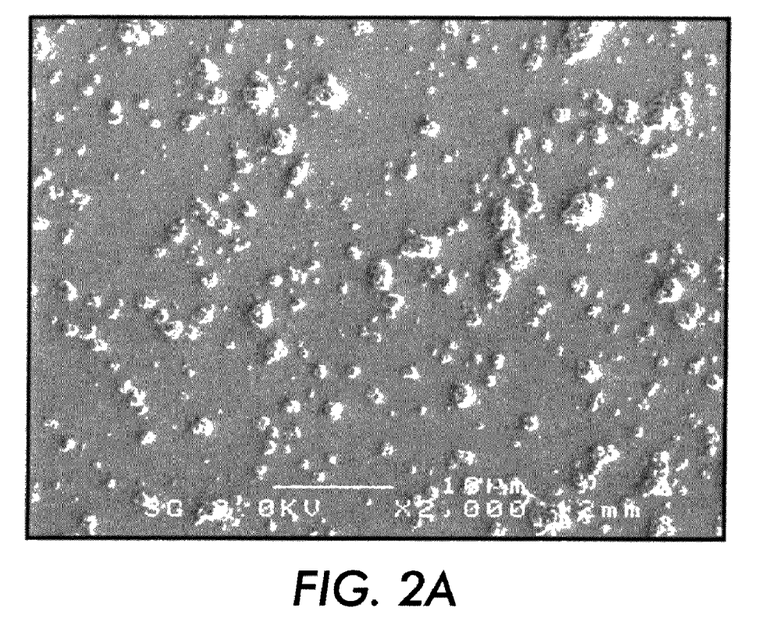
FIGS. 2A and 2B are scanning electron microscope (SEM) images of PTFE particles before (FIG. 2A) and after (FIG. 2B) formation of the core-shell.
Figure 2B:
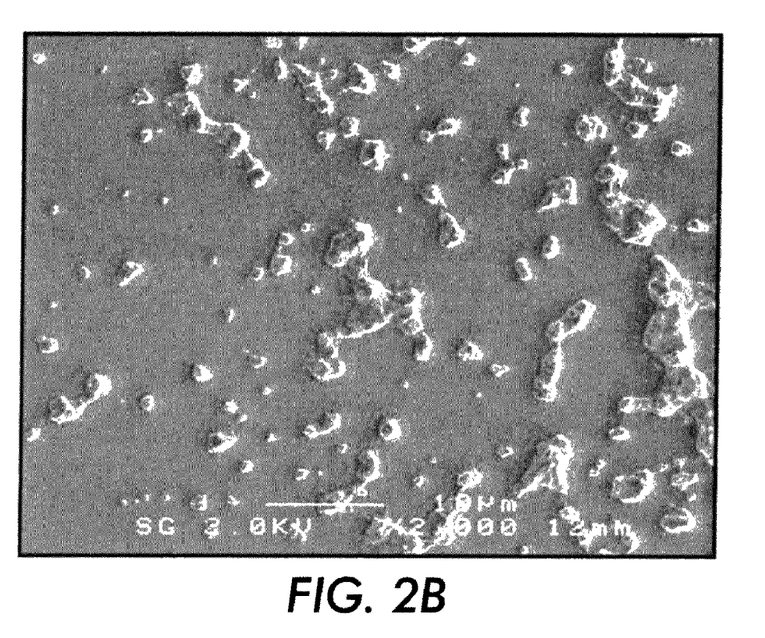

In specific embodiments, the core-shell fluorinated particles comprised PTFE. In such embodiments, overcoat layers with different PTFE loadings, for example from about 1 wt % to about 5 wt %, were achieved and tested. An overcoat layer with 5 wt % PTFE particles demonstrated a similar photoinduced discharge curve (PIDC) characteristic as the control overcoat layer without the PTFE loadings, but additionally demonstrated lower torque (e.g., lower friction with the cleaning blade) than the control overcoat layer. FIG. 2A is a SEM image showing bare PTFE particles of about 1 micron diameter size and FIG. 2B is a SEM image showing the melamine-shell PTFE particles on silicon substrate. As can be seen, FIGS. 2A-2B demonstrate how the method of the present embodiments increases particle size as well as encapsulate melamine on the surface of the PTFE particles.

Figure 3:
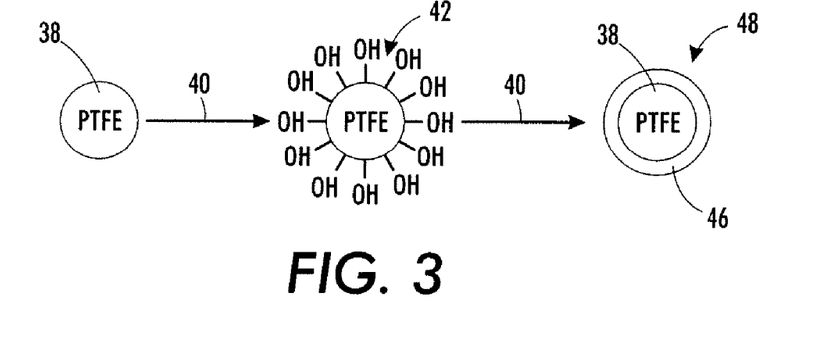
FIG. 3 is a schematic of the formation of core-shell fluorinated particles.

As illustrated by the schematic in FIG. 3, the core particles 38 were prepared by dispersing TEFLON/PTFE particles with hydroxyl-containing fluorinated dispersants 40, such as methacrylate-based fluorosurfactants, to obtain a suspension 42 in solvent. In one embodiment, the methacrylate-based fluorosurfactant has the following structure:

An amount of melamine-curing resin was added 44 and used to form a polymeric shell 46 around the core particle 38. In one embodiment, the melamine-curing resin has the following structure:

The thickness of the polymeric shell 46 is from about 10 nanometers to about 2 microns, uniformly around the core particle 38. Stable core-shell particles 48 in solvent, such as DOWANOL PM glycol ether (available from The Dow Chemical Co. (Midland, Mich.)), were thus obtained and utilized as torque reduction fillers for the present overcoat applications. Stable PTFE particle suspension in DOWANOL PM solvent was spin-coated for investigation of the PTFE particles.

The Substrate

The photoreceptor support substrate 10 may be opaque or substantially transparent, and may comprise any suitable organic or inorganic material having the requisite mechanical properties. The entire substrate can comprise the same material as that in the electrically conductive surface, or the electrically conductive surface can be merely a coating on the substrate. Any suitable electrically conductive material can be employed, such as for example, metal or metal alloy. Electrically conductive materials include copper, brass, nickel, zinc, chromium, stainless steel, conductive plastics and rubbers, aluminum, semitransparent aluminum, steel, cadmium, silver, gold, zirconium, niobium, tantalum, vanadium, hafnium, titanium, nickel, niobium, stainless steel, chromium, tungsten, molybdenum, paper rendered conductive by the inclusion of a suitable material therein or through conditioning in a humid atmosphere to ensure the presence of sufficient water content to render the material conductive, indium, tin, metal oxides, including tin oxide and indium tin oxide, and the like. It could be single metallic compound or dual layers of different metals and/or oxides.

The substrate 10 can also be formulated entirely of an electrically conductive material, or it can be an insulating material including inorganic or organic polymeric materials, such as MYLAR, a commercially available biaxially oriented polyethylene terephthalate from DuPont, or polyethylene naphthalate available as KALEDEX 2000, with a ground plane layer 12 comprising a conductive titanium or titanium/zirconium coating, otherwise a layer of an organic or inorganic material having a semiconductive surface layer, such as indium tin oxide, aluminum, titanium, and the like, or exclusively be made up of a conductive material such as, aluminum, chromium, nickel, brass, other metals and the like. The thickness of the support substrate depends on numerous factors, including mechanical performance and economic considerations.

The substrate 10 may have a number of many different configurations, such as for example, a plate, a cylinder, a drum, a scroll, an endless flexible belt, and the like. In the case of the substrate being in the form of a belt, as shown in FIG. 2, the belt can be seamed or seamless. In embodiments, the photoreceptor herein is in a drum configuration.

The thickness of the substrate 10 depends on numerous factors, including flexibility, mechanical performance, and economic considerations. The thickness of the support substrate 10 of the present embodiments may be at least about 500 microns, or no more than about 3,000 microns, or be at least about 750 microns, or no more than about 2500 microns.

An exemplary substrate support 10 is not soluble in any of the solvents used in each coating layer solution, is optically transparent or semi-transparent, and is thermally stable up to a high temperature of about 150° C. A substrate support 10 used for imaging member fabrication may have a thermal contraction coefficient ranging from about $1 \times 10^{-5}$ per ° C. to about $3 \times 10^{-5}$ per ° C. and a Young's Modulus of between about $5 \times 10^{-5}$ psi ($3.5 \times 10^{-4}$ Kg/cm$^2$) and about $7 \times 10^{-5}$ psi ($4.9 \times 10^{-4}$ Kg/cm$^2$).

The Ground Plane

The electrically conductive ground plane 12 may be an electrically conductive metal layer which may be formed, for example, on the substrate 10 by any suitable coating technique, such as a vacuum depositing technique. Metals include aluminum, zirconium, niobium, tantalum, vanadium, hafnium, titanium, nickel, stainless steel, chromium, tungsten, molybdenum, and other conductive substances, and mixtures thereof. The conductive layer may vary in thickness over substantially wide ranges depending on the optical transparency and flexibility desired for the electrophotoconductive member. Accordingly, for a flexible photoresponsive imaging device, the thickness of the conductive layer may be at least about 20 Angstroms, or no more than about 750 Angstroms, or at least about 50 Angstroms, or no more than about 200 Angstroms for an optimum combination of electrical conductivity, flexibility and light transmission.

Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive indium tin oxide as transparent layer for light having a wavelength between about 4000 Angstroms and about 9000 Angstroms or a conductive carbon black dispersed in a polymeric binder as an opaque conductive layer.

The Hole Blocking Layer

After deposition of the electrically conductive ground plane layer, the hole blocking layer 14 may be applied thereto. Electron blocking layers for positively charged photoreceptors allow holes from the imaging surface of the photoreceptor to migrate toward the conductive layer. For negatively charged photoreceptors, any suitable hole blocking layer capable of forming a barrier to prevent hole injection from the conductive layer to the opposite photoconductive layer may be utilized. The hole blocking layer may include polymers such as polyvinylbutryral, epoxy resins, polyesters, polysiloxanes, polyamides, polyurethanes and the like, or may be nitrogen containing siloxanes or nitrogen containing titanium compounds such as trimethoxysilyl propylene diamine, hydrolyzed trimethoxysilyl propyl ethylene diamine, N-beta-(aminoethyl) gamma-amino-propyl trimethoxy silane, isopropyl 4-aminobenzene sulfonyl, di(dodecylbenzene sulfonyl) titanate, isopropyl di(4-aminobenzoyl)isostearoyl titanate, isopropyl tri(N-ethylamino-ethylamino)titanate, isopropyl trianthranil titanate, isopropyl tri(N,N-dimethylethylamino)titanate, titanium-4-amino benzene sulfonate oxyacetate, titanium 4-aminobenzoate isostearate oxyacetate, $[H_2N(CH_2)_4]CH_3Si(OCH_3)_2$, (gamma-aminobutyl) methyl diethoxysilane, and $[H_2N(CH_2)_3]CH_3Si(OCH_3)_2$ (gamma-aminopropyl)methyl diethoxysilane, as disclosed in U.S. Pat. Nos. 4,338,387, 4,286,033 and 4,291,110.

General embodiments of the undercoat layer may comprise a metal oxide and a resin binder. The metal oxides that can be used with the embodiments herein include, but are not limited to, titanium oxide, zinc oxide, tin oxide, aluminum oxide, silicon oxide, zirconium oxide, indium oxide, molybdenum oxide, and mixtures thereof. Undercoat layer binder materials may include, for example, polyesters, MOR-ESTER 49,000 from Morton International Inc., VITEL PE-100, VITEL PE-200, VITEL PE-200D, and VITEL PE-222 from Goodyear Tire and Rubber Co., polyarylates such as ARDEL from AMOCO Production Products, polysulfone from AMOCO Production Products, polyurethanes, and the like.

The hole blocking layer should be continuous and have a thickness of less than about 0.5 micron because greater thicknesses may lead to undesirably high residual voltage. A hole blocking layer of between about 0.005 micron and about 0.3 micron is used because charge neutralization after the exposure step is facilitated and optimum electrical performance is achieved. A thickness of between about 0.03 micron and about 0.06 micron is used for hole blocking layers for optimum electrical behavior. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layer is applied in the form of a dilute solution, with the solvent being removed after deposition of the coating by conventional techniques such as by vacuum, heating and the like. Generally, a weight ratio of hole blocking layer material and solvent of between about 0.05:100 to about 0.5:100 is satisfactory for spray coating.

The Charge Generation Layer

The charge generation layer 18 may thereafter be applied to the undercoat layer 14. Any suitable charge generation binder including a charge generating/photoconductive material, which may be in the form of particles and dispersed in a film forming binder, such as an inactive resin, may be utilized. Examples of charge generating materials include, for example, inorganic photoconductive materials such as amorphous selenium, trigonal selenium, and selenium alloys selected from the group consisting of selenium-tellurium, selenium-tellurium-arsenic, selenium arsenide and mixtures thereof, and organic photoconductive materials including various phthalocyanine pigments such as the X-form of metal free phthalocyanine, metal phthalocyanines such as vanadyl phthalocyanine and copper phthalocyanine, hydroxy gallium phthalocyanines, chlorogallium phthalocyanines, titanyl phthalocyanines, quinacridones, dibromo anthanthrone pigments, benzimidazole perylene, substituted 2,4-diamino-triazines, polynuclear aromatic quinones, enzimidazole perylene, and the like, and mixtures thereof, dispersed in a film forming polymeric binder. Selenium, selenium alloy, benzimidazole perylene, and the like and mixtures thereof may be formed as a continuous, homogeneous charge generation layer. Benzimidazole perylene compositions are well known and described, for example, in U.S. Pat. No. 4,587,189, the entire disclosure thereof being incorporated herein by reference. Multi-charge generation layer compositions may be used where a photoconductive layer enhances or reduces the properties of the charge generation layer. Other suitable charge generating materials known in the art may also be utilized, if desired. The charge generating materials selected should be sensitive to activating radiation having a wavelength between about 400 and about 900 nm during the imagewise radiation exposure step in an electrophotographic imaging process to form an electrostatic latent image. For example, hydroxygallium phthalocyanine absorbs light of a wavelength of from about 370 to about 950 nanometers, as disclosed, for example, in U.S. Pat. No. 5,756,245.

A number of titanyl phthalocyanines, or oxytitanium phthalocyanines for the photoconductors illustrated herein are photogenerating pigments known to absorb near infrared light around 800 nanometers, and may exhibit improved sensitivity compared to other pigments, such as, for example, hydroxygallium phthalocyanine. Generally, titanyl phthalocyanine is known to have five main crystal forms known as Types I, II, III, X, and IV. For example, U.S. Pat. Nos. 5,189,155 and 5,189,156, the disclosures of which are totally incorporated herein by reference, disclose a number of methods for obtaining various polymorphs of titanyl phthalocyanine. Additionally, U.S. Pat. Nos. 5,189,155 and 5,189,156 are directed to processes for obtaining Types I, X, and IV phthalocyanines. U.S. Pat. No. 5,153,094, the disclosure of which is totally incorporated herein by reference, relates to the preparation of titanyl phthalocyanine polymorphs including Types I, II, III, and IV polymorphs. U.S. Pat. No. 5,166,339, the disclosure of which is totally incorporated herein by reference, discloses processes for preparing Types I, IV, and X titanyl phthalocyanine polymorphs, as well as the preparation of two polymorphs designated as Type Z-1 and Type Z-2.

Any suitable inactive resin materials may be employed as a binder in the charge generation layer 18, including those described, for example, in U.S. Pat. No. 3,121,006, the entire disclosure thereof being incorporated herein by reference. Organic resinous binders include thermoplastic and thermosetting resins such as one or more of polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl butyral, polyvinyl acetate, polysiloxanes, polyacrylates, polyvinyl acetals, polyamides, polyimides, amino resins, phenylene oxide resins, terephthalic acid resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride/vinylchloride copolymers, vinylacetate/vinylidene chloride copolymers, styrene-alkyd resins, and the like. Another film-forming polymer binder is PCZ-400 (poly (4,4'-dihydroxy-diphenyl-1-1-cyclohexane) which has a viscosity-molecular weight of 40,000 and is available from Mitsubishi Gas Chemical Corporation (Tokyo, Japan).

The charge generating material can be present in the resinous binder composition in various amounts. Generally, at least about 5 percent by volume, or no more than about 90 percent by volume of the charge generating material is dispersed in at least about 95 percent by volume, or no more than about 10 percent by volume of the resinous binder, and more specifically at least about 20 percent, or no more than about 60 percent by volume of the charge generating material is dispersed in at least about 80 percent by volume, or no more than about 40 percent by volume of the resinous binder composition.

In specific embodiments, the charge generation layer 18 may have a thickness of at least about 0.1 µm, or no more than about 2 µm, or of at least about 0.2 µm, or no more than about 1 µm. These embodiments may be comprised of chlorogallium phthalocyanine or hydroxygallium phthalocyanine or mixtures thereof. The charge generation layer 18 containing the charge generating material and the resinous binder material generally ranges in thickness of at least about 0.1 µm, or no more than about 5 µm, for example, from about 0.2 µm to about 3 µm when dry. The charge generation layer thickness is generally related to binder content. Higher binder content compositions generally employ thicker layers for charge generation.

The Charge Transport Layer

In a drum photoreceptor, the charge transport layer comprises a single layer of the same composition. As such, the charge transport layer will be discussed specifically in terms of a single layer 20, but the details will be also applicable to an embodiment having dual charge transport layers. The charge transport layer 20 is thereafter applied over the charge generation layer 18 and may include any suitable transparent organic polymer or non-polymeric material capable of supporting the injection of photogenerated holes or electrons from the charge generation layer 18 and capable of allowing the transport of these holes/electrons through the charge transport layer to selectively discharge the surface charge on the imaging member surface. In one embodiment, the charge transport layer 20 not only serves to transport holes, but also protects the charge generation layer 18 from abrasion or chemical attack and may therefore extend the service life of the imaging member. The charge transport layer 20 can be a substantially non-photoconductive material, but one which supports the injection of photogenerated holes from the charge generation layer 18.

The layer 20 is normally transparent in a wavelength region in which the electrophotographic imaging member is to be used when exposure is affected there to ensure that most of the incident radiation is utilized by the underlying charge generation layer 18. The charge transport layer should exhibit excellent optical transparency with negligible light absorption and no charge generation when exposed to a wavelength of light useful in xerography, e.g., 400 to 900 nanometers. In the case when the photoreceptor is prepared with the use of a transparent substrate 10 and also a transparent or partially transparent conductive layer 12, image wise exposure or erase may be accomplished through the substrate 10 with all light passing through the back side of the substrate. In this case, the materials of the layer 20 need not transmit light in the wavelength region of use if the charge generation layer 18 is sandwiched between the substrate and the charge transport layer 20. The charge transport layer 20 in conjunction with the charge generation layer 18 is an insulator to the extent that an electrostatic charge placed on the charge transport layer is not conducted in the absence of illumination. The charge transport layer 20 should trap minimal charges as the charge passes through it during the discharging process.

The charge transport layer 20 may include any suitable charge transport component or activating compound useful as an additive dissolved or molecularly dispersed in an electrically inactive polymeric material, such as a polycarbonate binder, to form a solid solution and thereby making this material electrically active. "Dissolved" refers, for example, to forming a solution in which the small molecule is dissolved in the polymer to form a homogeneous phase; and molecularly dispersed in embodiments refers, for example, to charge transporting molecules dispersed in the polymer, the small molecules being dispersed in the polymer on a molecular scale. The charge transport component may be added to a film forming polymeric material which is otherwise incapable of supporting the injection of photogenerated holes from the charge generation material and incapable of allowing the transport of these holes through. This addition converts the electrically inactive polymeric material to a material capable of supporting the injection of photogenerated holes from the charge generation layer 18 and capable of allowing the transport of these holes through the charge transport layer 20 in order to discharge the surface charge on the charge transport layer. The high mobility charge transport component may comprise small molecules of an organic compound which cooperate to transport charge between molecules and ultimately to the surface of the charge transport layer. For example, but not limited to, N,N'-diphenyl-N,N-bis(3-methyl phenyl)-1,1'-biphenyl-4,4'-diamine (TPD), other arylamines like triphenyl amine, N,N,N',N'-tetra-p-tolyl-1,1'-biphenyl-4,4'-diamine (TM-TPD), and the like.

A number of charge transport compounds can be included in the charge transport layer, which layer generally is of a thickness of from about 5 to about 75 microns, and more specifically, of a thickness of from about 15 to about 40 microns. Examples of charge transport components are aryl amines of the following formulas/structures:

wherein X is a suitable hydrocarbon like alkyl, alkoxy, aryl, and derivatives thereof; a halogen, or mixtures thereof, and especially those substituents selected from the group consisting of Cl and CH$_3$; and molecules of the following formulas and wherein X, Y and Z are independently alkyl, alkoxy, aryl, a halogen, or mixtures thereof, and wherein at least one of Y and Z are present.

Alkyl and alkoxy contain, for example, from 1 to about 25 carbon atoms, and more specifically, from 1 to about 12 carbon atoms, such as methyl, ethyl, propyl, butyl, pentyl, and the corresponding alkoxides. Aryl can contain from 6 to about 36 carbon atoms, such as phenyl, and the like. Halogen includes chloride, bromide, iodide, and fluoride. Substituted alkyls, alkoxys, and aryls can also be selected in embodiments.

Examples of specific aryl amines that can be selected for the charge transport layer include N,N'-diphenyl-N,N'-bis(alkylphenyl)-1,1-biphenyl-4,4'-diamine wherein alkyl is selected from the group consisting of methyl, ethyl, propyl, butyl, hexyl, and the like; N,N'-diphenyl-N,N'-bis(halophenyl)-1,1'-biphenyl-4,4'-diamine wherein the halo substituent is a chloro substituent; N,N'-bis(4-butylphenyl)-N,N'-di-p-tolyl-[p-terphenyl]-4,4"-diamine, N,N'-bis(4-butylphenyl)-N,N'-di-m-tolyl-[p-terphenyl]-4,4"-diamine, N,N'-bis(4-butylphenyl)-N,N'-di-o-tolyl[p-terphenyl]-4,4"-diamine, N,N'-bis(4-butylphenyl)-N,N'-bis-(4-isopropylphenyl)-[p-terphenyl]-4,4"-diamine, N,N'-bis(4-butylphenyl)-N,N'-bis-(2-ethyl-6-methylphenyl)-[p-terphenyl]-4,4"-diamine, N,N'-bis(4-butylphenyl)-N,N'-bis-(2,5-dimethylphenyl)-[p-terphenyl]-4,4'-diamine, N,N'-diphenyl-N,N'-bis(3-chlorophenyl)-[p-terphenyl]-4,4"-diamine, and the like. Other known charge transport layer molecules may be selected in embodiments, reference for example, U.S. Pat. Nos. 4,921,773 and 4,464,450, the disclosures of which are totally incorporated herein by reference.

Examples of the binder materials selected for the charge transport layers include components, such as those described in U.S. Pat. No. 3,121,006, the disclosure of which is totally incorporated herein by reference. Specific examples of polymer binder materials include polycarbonates, polyarylates, acrylate polymers, vinyl polymers, cellulose polymers, polyesters, polysiloxanes, polyamides, polyurethanes, poly(cyclo olefins), and epoxies, and random or alternating copolymers thereof. In embodiments, the charge transport layer, such as a hole transport layer, may have a thickness of at least about 10 µm, or no more than about 40 µm.

Examples of components or materials optionally incorporated into the charge transport layers or at least one charge transport layer to, for example, enable improved lateral charge migration (LCM) resistance include hindered phenolic antioxidants such as tetrakis methylene(3,5-di-tert-butyl-4-hydroxy hydrocinnamate) methane (IRGANOX® 1010, available from Ciba Specialty Chemical), butylated hydroxytoluene (BHT), and other hindered phenolic antioxidants including SUMILIZER™ BHT-R, MDP-S, BBM-S, WX-R, NR, BP-76, BP-101, GA-80, GM and GS (available from Sumitomo Chemical Co., Ltd.), IRGANOX® 1035, 1076, 1098, 1135, 1141, 1222, 1330, 1425WL, 1520L, 245, 259, 3114, 3790, 5057 and 565 (available from Ciba Specialties Chemicals), and ADEKA STAB™ AO-20, AO-30, AO-40, AO-50, AO-60, AO-70, AO-80 and AO-330 (available from Asahi Denka Co., Ltd.); hindered amine antioxidants such as SANOL™ LS-2626, LS-765, LS-770 and LS-744 (available from SANKYO CO., Ltd.), TINUVIN® 144 and 622LD (available from Ciba Specialties Chemicals), MARK™ LA57, LA67, LA62, LA68 and LA63 (available from Asahi Denka Co., Ltd.), and SUMILIZER® TPS (available from Sumitomo Chemical Co., Ltd.); thioether antioxidants such as SUMILIZER® TP-D (available from Sumitomo Chemical Co., Ltd); phosphite antioxidants such as MARK™ 2112, PEP-8, PEP-24G, PEP-36, 329K and HP-10 (available from Asahi Denka Co., Ltd.); other molecules such as bis(4-diethylamino-2-methylphenyl)phenylmethane (BDETPM), bis-[2-methyl-4-(N-2-hydroxyethyl-N-ethyl-aminophenyl)]-phenylmethane (DHTPM), and the like. The weight percent of the antioxidant in at least one of the charge transport layer is from about 0 to about 20, from about 1 to about 10, or from about 3 to about 8 weight percent.

In embodiments where the outer layer is the charge transport layer, the micron-sized PTFE, particles can be incorporated into the charge transport formulation to provide an efficient manner to reduce friction between photoreceptor and cleaning blade. The core-shell fluorinated particles shows well-dispersed behavior in the charge transport layer formulation, good coating quality, and no negative electrical effect. Thus, like for the overcoat layer formulations, stable coating dispersions are facilitated by incorporating core-shell fluorinated particles, such as for example, core-shell TEFLON or PTFE nano- or micro-particles, into the charge transport layer. The core-shell particles have a polymeric shell made of melamine resin surrounding the fluoro-polymer core. Charge transport layers having such compositions have shown to provide longer service life as well as avoid print defects due to cleaning failures.

The charge transport layer should be an insulator to the extent that the electrostatic charge placed on the hole transport layer is not conducted in the absence of illumination at a rate sufficient to prevent formation and retention of an electrostatic latent image thereon. The charge transport layer is substantially nonabsorbing to visible light or radiation in the region of intended use, but is electrically "active" in that it allows the injection of photogenerated holes from the photoconductive layer, that is the charge generation layer, and allows these holes to be transported through itself to selectively discharge a surface charge on the surface of the active layer.

Any suitable and conventional technique may be utilized to form and thereafter apply the charge transport layer mixture to the supporting substrate layer. The charge transport layer may be formed in a single coating step or in multiple coating steps. Dip coating, ring coating, spray, gravure or any other drum coating methods may be used.

Drying of the deposited coating may be effected by any suitable conventional technique such as oven drying, infra red radiation drying, air drying and the like. The thickness of the charge transport layer after drying is from about 10 μM to about 40 μm or from about 12 μm to about 36 μm for optimum photoelectrical and mechanical results. In another embodiment the thickness is from about 14 μm to about 36 μm.

The Adhesive Layer

An optional separate adhesive interface layer may be provided in certain configurations, such as for example, in flexible web configurations. In the embodiment illustrated in FIG. 1, the interface layer would be situated between the blocking layer 14 and the charge generation layer 18. The interface layer may include a copolyester resin. Exemplary polyester resins which may be utilized for the interface layer include polyarylatepolyvinylbutyrals, such as ARDEL POLYARYLATE (U-100) commercially available from Toyota Hsutsu Inc., VITEL PE-100, VITEL PE-200, VITEL PE-200D, and VITEL PE-222, all from Bostik, 49,000 polyester from Rohm Hass, polyvinyl butyral, and the like. The adhesive interface layer may be applied directly to the hole blocking layer 14. Thus, the adhesive interface layer in embodiments is in direct contiguous contact with both the underlying hole blocking layer 14 and the overlying charge generator layer 18 to enhance adhesion bonding to provide linkage. In yet other embodiments, the adhesive interface layer is entirely omitted.

Any suitable solvent or solvent mixtures may be employed to form a coating solution of the polyester for the adhesive interface layer. Solvents may include tetrahydrofuran, toluene, monochlorobenzene, methylene chloride, cyclohexanone, and the like, and mixtures thereof. Any other suitable and conventional technique may be used to mix and thereafter apply the adhesive layer coating mixture to the hole blocking layer. Application techniques may include spraying, dip coating, roll coating, wire wound rod coating, and the like. Drying of the deposited wet coating may be effected by any suitable conventional process, such as oven drying, infra red radiation drying, air drying, and the like.

The adhesive interface layer may have a thickness of at least about 0.01 microns, or no more than about 900 microns after drying. In embodiments, the dried thickness is from about 0.03 microns to about 1 micron.

The Ground Strip

The ground strip may comprise a film forming polymer binder and electrically conductive particles. Any suitable electrically conductive particles may be used in the electrically conductive ground strip layer 19. The ground strip 19 may comprise materials which include those enumerated in U.S. Pat. No. 4,664,995. Electrically conductive particles include carbon black, graphite, copper, silver, gold, nickel, tantalum, chromium, zirconium, vanadium, niobium, indium tin oxide and the like. The electrically conductive particles may have any suitable shape. Shapes may include irregular, granular, spherical, elliptical, cubic, flake, filament, and the like. The electrically conductive particles should have a particle size less than the thickness of the electrically conductive ground strip layer to avoid an electrically conductive ground strip layer having an excessively irregular outer surface. An average particle size of less than about 10 microns generally avoids excessive protrusion of the electrically conductive particles at the outer surface of the dried ground strip layer and ensures relatively uniform dispersion of the particles throughout the matrix of the dried ground strip layer. The concentration of the conductive particles to be used in the ground strip depends on factors such as the conductivity of the specific conductive particles utilized.

The ground strip layer may have a thickness of at least about 7 microns, or no more than about 42 microns, or of at least about 14 microns, or no more than about 27 microns.

The Anti-Curl Back Coating Layer

The anti-curl back coating 1 may comprise organic polymers or inorganic polymers that are electrically insulating or slightly semi-conductive. The anti-curl back coating provides flatness and/or abrasion resistance.

Anti-curl back coating 1 may be formed at the back side of the substrate 2, opposite to the imaging layers. The anti-curl back coating may comprise a film forming resin binder and an adhesion promoter additive. The resin binder may be the same resins as the resin binders of the charge transport layer discussed above. Examples of film forming resins include polyacrylate, polystyrene, bisphenol polycarbonate, poly(4,4'-isopropylidene diphenyl carbonate), 4,4'-cyclohexylidene diphenyl polycarbonate, and the like. Adhesion promoters used as additives include 49,000 (du Pont), Vitel PE-100, Vitel PE-200, Vitel PE-307 (Goodyear), and the like. Usually from about 1 to about 15 weight percent adhesion promoter is selected for film forming resin addition. The thickness of the anti-curl back coating is at least about 3 microns, or no more than about 35 microns, or about 14 microns.

In addition, in the present embodiments using a belt configuration, the charge transport layer may consist of a single pass charge transport layer or a dual pass charge transport layer (or dual layer charge transport layer) with the same or different transport molecule ratios. In these embodiments, the dual layer charge transport layer has a total thickness of from about 10 μm to about 40 μm. In other embodiments, each layer of the dual layer charge transport layer may have an individual thickness of from 2 μm to about 20 μm. Moreover, the charge transport layer may be configured such that it is used as a top layer of the photoreceptor to inhibit crystallization at the interface of the charge transport layer and the overcoat layer. In another embodiment, the charge transport layer may be configured such that it is used as a first pass charge transport layer to inhibit microcrystallization occurring at the interface between the first pass and second pass layers.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Example 1

Preparation of the Core-Shell Fluorinated Particles

PTFE particles with about 1 micron diameter size were used. 5 wt % of PTI-E, particles were successfully suspended in DOWANOL PM with a perfluoro-surfactant (GF-300, available from Toagosei America, Inc. (West Jefferson, Ohio)) at 0.5 wt %. CYMEL 303 was added to the suspension to form the core-shell particles. The amount of CYMEL 303 was controlled (CYMEL/PTFE=1/1, 2/1, 5/1) and added with 0.1% of an acid catalyst such as p-toluenesulfonic acid. All samples demonstrated good stability in DOWANOL PM with GF-300 surfactant. However, the core-shell PTFE samples show best stability after 2 days of resting, for example, after the rest of the PTFE samples showed settlement.

Fabrication of Cylinder/Drum-type Photoreceptor with Overcoat Layer Containing Core-shell Fluorinated Particles:

An electrophotographic photoreceptor was fabricated in the following manner. A coating solution for an undercoat layer comprising 100 parts of a ziconium compound (trade name: Orgatics ZC540), 10 parts of a silane compound (trade name: A110, manufactured by Nippon Unicar Co., Ltd), 400 parts of isopropanol solution and 200 parts of butanol was prepared. The coating solution was applied onto a cylindrical aluminum (Al) substrate subjected to honing treatment by dip coating, and dried by heating at 150° C. for 10 minutes to form an undercoat layer having a film thickness of 0.1 micrometer.

A 0.5 micron thick charge generating layer was subsequently dip coated on top of the undercoat layer from a dispersion of Type V hydroxygallium phthalocyanine (12 parts), alkylhydroxy gallium phthalocyanine (3 parts), and a vinyl chloride/vinyl acetate copolymer, VMCH (Mn=27,000, about 86 weight percent of vinyl chloride, about 13 weight percent of vinyl acetate and about 1 weight percent of maleic acid) available from Dow Chemical (10 parts), in 475 parts of n-butylacetate.

Subsequently, a 25 µm thick charge transport layer (CTL) was dip coated on top of the charge generating layer from a solution of N,N'-diphenyl-N,N'-bis(3-methylphenyl)-1,1'-biphenyl-4,4'-diamine (82.3 parts), 2.1 parts of 2,6-di-tert-butyl-4-methylphenol (BHT) from Aldrich and a polycarbonate, PCZ-400 [poly(4,4'-dihydroxy-diphenyl-1-1-cyclohexane), $M_w$=40,000] available from Mitsubishi Gas Chemical Company, Ltd. (123.5 parts) in a mixture of 546 parts of tetrahydrofuran (THF) and 234 parts of monochlorobenzene. The CTL was dried at 115° C. for 60 minutes.

An overcoat formulation was prepared from a mixture of an acrylic polyol (1.5 parts, JONCRYL-587, available from Johnson Polymers LLC, Sturtevant, Wis., USA), a melamine resin (2.1 parts, CYMEL-303 available from Cytec Industries, Inc. West Paterson, N.J., USA), a charge transport component of N,N,N',N'-tetrakis-[(4-hydroxymethyl)phenyl]-biphenyl-4,4'-diamine (THM-TBD)(1.16 parts)/N,N'-diphenyl-N,N'-di(3-hydroxyphenyl)-terphenyl-diamine (DHTER)(1.93 pats), and an acid catalyst (0.05 part, Nacure 5225 available from King Chemical Industries), in a solvent of 1-methoxy-2-propanol (20.9 parts).

Core-shell PTFE particles were added to the overcoat formulation such that the PTFE loading was 5 wt % core-shell PTFE. The formulation was cup-coated on a drum photoreceptor. For comparison, a control photoreceptor was prepared with the same above-described overcoat formulation but without any core-shell PTFE particles.

The solution was applied onto the photoreceptor surface and more specifically onto the charge transport layer, using cup coating technique. Finally thermal curing was done at 140° C. for 40 minutes to form an overcoat layer having an average film thickness of about 6 µm.

Results

Figure 4:
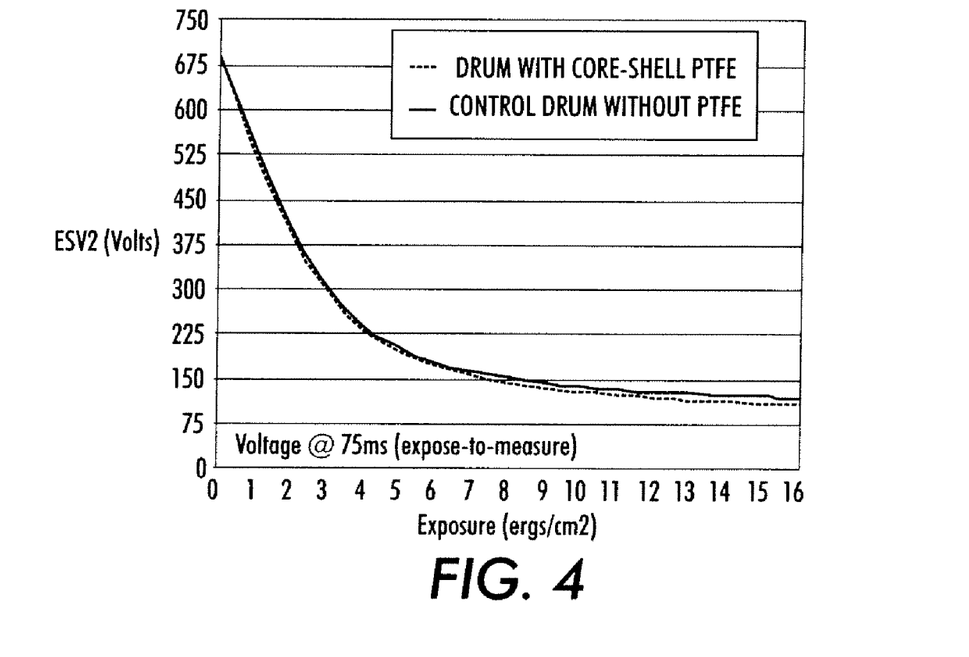
FIG. 4 is a graph illustrating a comparison of the electrical performance of a control photoreceptor and a photoreceptor made according to the present embodiments.

Evaluation of Electrophotographic Photoreceptor Performance:

The electrical performance characteristics of the above prepared electrophotographic photoreceptors such as electrophotographic sensitivity and short term cycling stability were tested in a scanner. The scanner is known in the industry and equipped with means to rotate the drum while it is electrically charged and discharged. The charge on the photoconductor sample is monitored through use of electrostatic probes placed at precise positions around the circumference of the device. The photoreceptor devices are charged to a negative potential of 500 Volts. As the devices rotate, the initial charging potentials are measured by voltage probe 1. The photoconductor samples are then exposed to monochromatic radiation of known intensity, and the surface potential measured by voltage probes 2 and 3. Finally, the samples are exposed to an erase lamp of appropriate intensity and wavelength and any residual potential is measure by voltage probe 4. The process is repeated under the control of the scanner's computer, and the data is stored in the computer. The PIDC (photo induced discharge curve) is obtained by plotting the potentials at voltage probes 2 and 3 as a function of the light energy. All the photoreceptors as prepared in Examples 1 showed similar PIDC characteristics as the control or Comparative Example device. The test results demonstrate that the electrical performance of the samples with core-shell fluorinated particles is nearly same with that of the control sample without the particles. As shown in FIG. 4, the inventive drum exhibited similar PIDC characteristics as the control drum, thus demonstrating that the incorporation of the core-shell particles did not have a negative impact on electrical performance.

Figure 5:
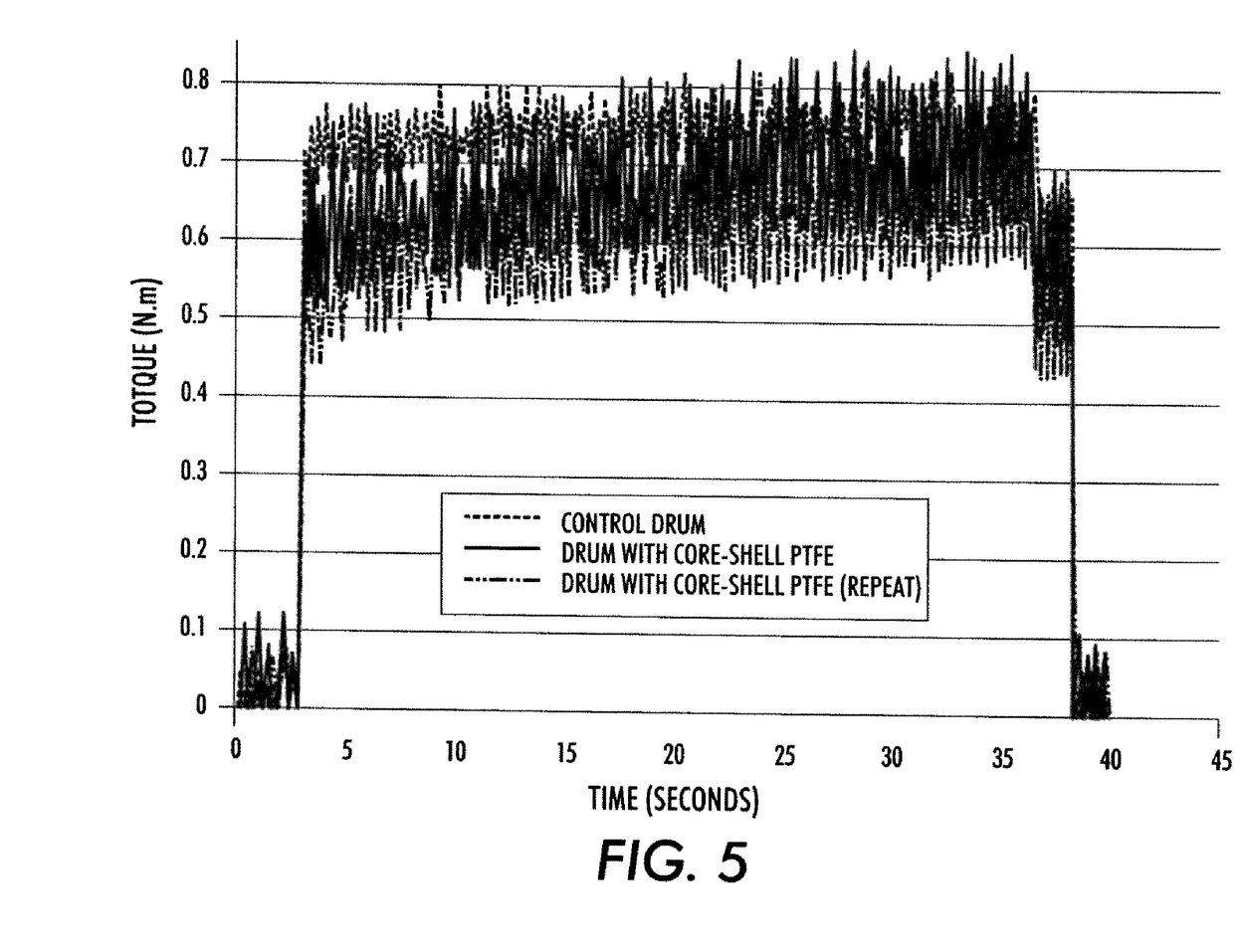
FIG. 5 is a graph illustrating a comparison of the torque measurements of a control photoreceptor and photoreceptors made according to the present embodiments.

Torque Measurements:

Torque measurements were made on a control drum without core-shell PTFE particles, and two drums with 5 wt % core-shell PTFE particles. Multiple measurements were made and averaged. The results, as shown in FIG. 5, clearly indicate that core-shell PTFE containing drums show lower torque than the control drum without core-shell PTFE particles.

Future optimization on the design of size of the particular is possible for maximum torque reduction. Initial print tests showed good solid-area, halftone and line reproduction, similar to the control. No major print defect occurred to the presence of the core-shell fluorinated particles in overcoat layer.

In summary, the present embodiments provide for a novel overcoat layer comprising core-shell TEFLON/PTFE nano- or micro-particles which has been demonstrated to facilitate reduced torque and avoid print defects due to cleaning failures. The test results also demonstrated that there is no electrically negative effect caused by or associated with the addition of the core-shell fluorinated particles into the overcoat formulation.

All the patents and applications referred to herein are hereby specifically, and totally incorporated herein by reference in their entirety in the instant specification.

It will be appreciated that several of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. An imaging member comprising:
   a substrate,
   an imaging layer disposed on the substrate, and
   an outer layer disposed on the imaging layer, wherein the outer layer further comprises a plurality of core-shell fluorinated particles comprising a fluoro-polymer core having a polymeric shell disposed on the fluoro-polymer core and further wherein the fluoro-polymer comprises a polymer having at least a monomer repeat unit selected from the group consisting of tetrafluoroethylene, vinylidene fluoride, hexafluoropropylene, perfluoro(methyl vinyl ether), perfluoro(ethyl vinyl ether), perfluoro(propyl vinyl ether), and mixtures thereof.

2. The imaging member of claim 1, wherein fluoro-polymer is selected from a group consisting of polytetrafluoroethylene (PTFE), a copolymer of tetrafluoroethylene (TFE) and hexafluoropropylene (HFP), a copolymer of hexafluoropropylene (HFP) and vinylidene fluoride (VDF), a copolymer of hexafluoropropylene (HFP) and vinylidene fluoride (VF2), a terpolymer of tetrafluoroethylene (TFE), vinylidene fluoride (VDF), and hexafluoropropylene (HFP), and a tetrapolymer of tetrafluoroethylene (TFE), vinylidene fluoride (VF2), and hexafluoropropylene (HFP).

3. The imaging member of claim 1, wherein the polymeric shell comprises a crosslinked product of a hydroxyl-containing fluorinated dispersant and a curing agent selected from the group consisting of melamine-formaldehyde resin, phenol-formaldehyde resin, melamine-phenol-formaldehyde resin, guanamine-formaldehyde resin, an isocyanate compound or a masking isocyanate compound, a polyol resin, and mixtures thereof.

4. The imaging member of claim 3, wherein the hydroxyl-containing fluorinated dispersant comprises a polyacrylate polymer containing a hydroxyl group and a fluoroalkyl group having from about 6 to about 20 carbons.

5. The imaging member of claim 1, wherein the fluoro-polymer core has a diameter size ranging from about 20 nanometers to about 8 micrometers.

6. The imaging member of claim 1, wherein the polymeric shell has a thickness of from about 5 nanometers to about 2 microns.

7. The imaging member of claim 1, wherein the core-shell fluorinated particles are present in an amount of from about 1% to about 10% by weight of total weight of the outer layer.

8. The imaging member of claim 1, wherein the imaging layer has a multi-layered structure and further comprises a charge generation layer disposed on the substrate and a charge transport layer disposed on the charge generation layer, and further wherein the charge generation layer comprises a photosensitive pigment and the charge transport layer is the outer layer of the imaging member.

9. The imaging member of claim 8, wherein the photosensitive pigment is selected from the group consisting of metal free phthalocyanine, titanyl phthalocyanine, chlorogallium phthalocyanine, hydroxygallium phthalocyanine, a mixture of alkylhydroxy gallium phthalocyanine and hydroxygallium phthalocyanine, a perylene, and mixtures thereof, and further wherein the charge transport layer comprises a tertiary arylamine and a polymer binder.

10. The imaging member of claim 9, wherein the charge transport layer comprises a tertiary arylamine selected from the group consisting of N,N'-diphenyl-N,N'-bis(3-methylphenyl)-(1,1'-biphenyl)-4,4'-diamine, N,N'-diphenyl-N,N'-bis(4-methylphenyl)-(1,1'-biphenyl)-4,4'-diamine, N,N,N',N'-tetrakis(4-methylphenyl)-1,1'-biphenyl)-4,4'-diamine, N,N'-bis(4-butylphenyl)-N,N'-di-p-tolyl-[p-terphenyl]-4,4'-diamine, and N,N'-bis(4-butylphenyl)-N,N'-di-m-tolyl-[p-terphenyl]-4,4'-diamine, and mixtures thereof, and further wherein the polymer resin is selected from the group consisting of polycarbonates, polyesters, polystyrene, and mixtures thereof.

11. The imaging member of claim 1, wherein the imaging layer has a multi-layered structure and further comprises a charge generation layer disposed on the substrate, a charge transport layer disposed on the charge generation layer and an overcoat layer disposed on the charge transport layer, and further wherein the overcoat layer is the outer layer of the imaging member.

12. The imaging member of claim 11, wherein the a charge generation layer comprises a photosensitive pigment selected from the group consisting of metal free phthalocyanine, titanyl phthalocyanine, chlorogallium phthalocyanine, hydroxygallium phthalocyanine, a mixture of alkylhydroxy gallium phthalocyanine and hydroxygallium phthalocyanine, a perylene, and mixtures thereof, and further wherein the charge transport layer comprises a tertiary arylamine selected from the group consisting of N,N'-diphenyl-N,N'-bis(3-methylphenyl)-(1,1'-biphenyl)-4,4'-diamine, N,N'-diphenyl-N,N'-bis(4-methylphenyl)-(1,1'-biphenyl)-4,4'-diamine, N,N,N',N'-tetrakis(4-methylphenyl)-1,1'-biphenyl)-4,4'-diamine, N,N'-bis(4-butylphenyl)-N,N'-di-p-tolyl-[p-terphenyl]-4,4'-diamine, N,N'-bis(4-butylphenyl)-N,N'-di-m-tolyl-[p-terphenyl]-4,4'-diamine, and mixtures thereof.

13. The imaging member of claim 11, wherein the overcoat layer is comprised of a cross-linked product obtained by curing and polymerizing a charge transport component comprised of a tertiary arylamine having at least a curable functional group selected from the group consisting of a hydroxyl, a hydroxymethyl, an alkoxymethyl, a hydroxyalkyl having from 1 to about 15 carbons, an acrylate, and mixtures thereof.

14. The imaging member of claim 13, wherein an additional curing agent is added for forming the cross-linked composition.

15. The imaging member of claim 14, wherein the curing agent is selected from the group consisting of a melamine-formaldehyde resin, a phenol resin, an isocyanate or a masking isocyanate compound, an acrylate resin, a polyol resin, and mixtures thereof.

16. An imaging forming apparatus comprising:
    an imaging member further comprising
       a substrate,
       an imaging layer disposed on the substrate, and
       an outer layer disposed on the imaging layer;
    a charging unit that applies electrostatic charge on the imaging member;
    a developing unit that develops toner image onto the imaging member;
    a transfer unit that transfers the toner image from the imaging member to a media; and
    a cleaning unit that cleans the imaging member,
    wherein the outer layer of the imaging member further comprises a plurality of core-shell fluorinated particles comprising a fluoro-polymer core having a polymeric shell disposed on the fluoro-polymer core and further wherein the fluoro-polymer comprises a polymer having at least a monomer repeat unit selected from the group consisting of tetrafluoroethylene, vinylidene fluoride, hexafluoropropylene, perfluoro(methyl vinyl ether), perfluoro(ethyl vinyl ether), and perfluoro(propyl vinyl ether), and mixtures thereof.

17. The imaging forming apparatus of claim 16, wherein the polymeric shell comprises a crosslinked product of a hydroxyl-containing fluorinated dispersant and a curing agent selected from the group consisting of melamine-formaldehyde resin, phenol-formaldehyde resin, melamine-phenol-formaldehyde resin, guanamine-formaldehyde resin, an isocyanate or a masking isocyanate compound, a polyol resin, or the mixture thereof, and mixtures thereof.

18. The imaging forming apparatus of claim 17, wherein the hydroxyl-containing fluorinated dispersant comprises a polyacrylate polymer containing a hydroxyl group and a fluoroalkyl group having from about 6 to about 20 carbons.

* * * * *